| United States Patent [19] | [11] Patent Number: 4,743,549 |
| Mayr et al. | [45] Date of Patent: May 10, 1988 |

[54] HYDROGEN PEROXIDE-FORMING SARCOSINE OXIDASE

[75] Inventors: Ulrich Mayr, Rosenheim; Hans Möllering, Tutzing; Joachim Siedel, Bernried; Hans Seidel, Tutzing, all of Fed. Rep. of Germany

[73] Assignee: Boehringer Mannheim GmbH, Mannheim-Waldhof, Fed. Rep. of Germany

[21] Appl. No.: 868,262

[22] Filed: May 28, 1986

[30] Foreign Application Priority Data

May 29, 1985 [DE] Fed. Rep. of Germany ....... 3519218

[51] Int. Cl.$^4$ .......................... C12N 9/06; C12Q 1/26; C12R 1/01; C12R 1/14; C12R 1/465; C12R 1/625

[52] U.S. Cl. ....................................... 435/191; 435/25; 435/822; 435/841; 435/886; 435/908

[58] Field of Search ................... 435/191, 25

[56] References Cited

U.S. PATENT DOCUMENTS 4,216,292  8/1980  Ikuta et al. .......................... 435/191

FOREIGN PATENT DOCUMENTS 56-92790  7/1981  Japan .................................. 435/191

Primary Examiner—Lionel M. Shapiro
Attorney, Agent, or Firm—Felfe & Lynch

[57] ABSTRACT

The present invention provides a hydrogen peroxide-forming sarcosine oxidase, wherein it is obtainable from Streptomycetaceae and at 25° C. in 0.15 mol/liter potassium phosphate (pH 7.9), in the presence of surface-active substances, still shows after 2 days an activity of at least 40% of the initial activity.

4 Claims, No Drawings

HYDROGEN PEROXIDE-FORMING SARCOSINE OXIDASE

The present invention is concerned with a new sarcosine oxidase with improved stability in comparison with known sarcosine oxidases, especially in detergent-containing analysis reagents.

Sarcosine oxidases (E.C. 1.5.3.1) can be used, inter alia, for the enzymatic determination of sarcosine, creatine and creatinine, the enzymatic determination of creatinine in serum, plasma or urine being of especial importance in clinical diagnosis. By coupling of the reactions catalysed by creatinine amidohydrolase (E.C. 3.5.2.10), creatine amidinohydrolase (E.C. 3.5.3.3) and sarcosine oxidase, hydrogen peroxide is finally formed from creatinine in the stoichiometric ratio of 1:1 and this can be determined colorimetrically in a simple way. Numerous chromogenic systems have proved to be especially useful for this colorimetric determination, for example those of the Trinder type (see Bergmeyer "Methoden der enzymatischen Analyse", 4th edition, Volume 1 (1983) page 197), in the case of which, in the presence of peroxidase, from 4-aminoantipyrine and a phenolic or anilinic coupler, a coloured material is produced oxidatively by hydrogen peroxide, the amount (or intensity) of this coloured material being in linear relationship to the amount of hydrogen peroxide formed.

Such a creatinine detection based upon the sarcosine reaction offers, in comparison with known enzymatic creatinine tests (Bergmeyer, "Methoden der enzymatischen Analyse", 3rd edition, Volume II (1974) page 1834, Tanganelli et al., Clin. Chem., 28, 1461/1983), the advantage, depending upon the nature of the colour coupler used, of a distinctly higher detection sensitivity which, precisely because of the low serum creatinine concentration in the diagnostically decisive range (44–97 μmol/l.), is of great importance for the exactitude of the analysis. In addition, the stability of the chromogenic substances in the neutral, aqueous medium employed is also better than that of NADH, the indicator used in UV tests. Also in comparison with the routine method even today used the most frequently, the creatinine determination according to Jaffé (Hoppe-Seyler's Z. Physiol. Chem., 10, 391/1886), this process also offers a substantially greater specificity and thus an improved diagnostic dependability. Finally, the use of corrosive, strongly alkaline reagents is thereby also avoided.

However, the use of sarcosine oxidase, for example for the determination of creatinine, requires that, in the reagent ready for use, it is sufficiently storage-stable for at least several days at 0° to 25° C. and, furthermore, in the case of carrying out the measurement even at elevated temperatures (30° to 37° C.), no significant loss of activity occurs over the minimum reaction time necessary. Since, in clinical chemistry, turbid, triglyceride-rich sera are frequently obtained as sample material, enzymatic analysis reagents preferably also contain so called clarification systems, most of which consist of a combination of lipases with non-ionic detergents (polyoxyethylated alkyl or aralkyl alcohols) and salts of bile acids, such as sodium cholate, as solubilising agent which permits the disturbance-free optical measurement even of strongly lipaemic samples.

In order, for example, also to be able to carry out the creatinine determination in such turbid samples, it is, therefore, necessary that the sarcosine oxidase, under the above-mentioned storage and reaction conditions, is sufficiently resistant towards denaturing or inactivation by detergents.

Furthermore, it is desirable that the sarcosine oxidase has appropriate enzymatic properties, for example a low Michaelis constant for sarcosine and a high maximum reaction rate, since, due to these properties, there is essentially co-determined the reaction time in the case of sarcosine, creatine and creatinine determinations. Since the enzymatic determination of, for example, creatinine is also to be capable of being carried out at higher temperatures (37° C.) and in the presence of detergents and solubilisers, appropriate enzymatic properties are of considerable importance in the case of these stressing ambient conditions.

Corresponding investigations showed that the known sarcosine oxidases in such detergent-containing analysis reagents do not display a storage stability satisfying these requirements and/or a stability at elevated reaction temperatures.

Therefore, there is a need for a sarcosine oxidase which possesses the above-mentioned properties and especially fulfils the stability criteria.

Thus, according to the present invention, there is provided a sarcosine oxidase obtainable from Streptomycetaceae which, at 25° C. in 0.15 mol/liter potassium phosphate (pH 7.9) and in the presence of surface-active substances, still shows after 2 days an activity of at least 40% of the initial activity.

At 37° C. in a detergent-containing medium, the sarcosine oxidase according to the present invention possesses for sarcosine a $K_M$ value of 2 to 4 mmol/liter. In contradistinction thereto, the $K_M$ values of the known sarcosine oxidases which are sufficiently stable for these determinations are, under these conditions, about 16 to 20 mmol/liter.

The enzyme according to the present invention is found in all species of the family Streptomycetacea (The Prokaryotes, Vol. II (1981), 2028), for example in *Chainia purpurogena* DSM 43 156, *Chainia ochraceae* DSM 43 155, *Streptomyces flocculus* DMS 40 327, Streptoverticillium sp. DSM 40 237) and *Kitasatoa purpurea* DMS 43 362.

The enzyme of the present invention is composed of four different sub-units and its molecular weight is about 170 kD.

The enzyme is stable in the pH range of 6 to 9 and at temperatures below 40° C. At 50° C., it is inactivated within 15 minutes. The optimum temperature of the reaction is about 37° C. and the pH optimum is pH 8.0. The high substrate specifically is shown by the very low conversion of substrate analogues; thus, the conversion rate of, for example, N,N-dimethylglycine is only 1% of that of the sarcosine-specific reaction.

The $K_M$ values for sarcosine (phosphate buffer; TES buffer), measured at 25° C. in various stressing reagents, are 2 to 3 mmol/liter. The $V_{max}$ is about 6 U/mg. protein. The following Table I gives, for various preparations of the enzyme according to the present invention, the $K_M$ values for sarcosine measured at 25° and at 37° C. For comparison, there are given the corresponding values for the known Bacillus enzyme.

TABLE I

| origin of the sarcosine oxidase | T (°C.) | buffer | $K_M$ value (mmol/l) for sarcosine in stressing reagent a |
|---|---|---|---|
| *Chainia purpurogena* (DSM 43 156) | | | |
| pure enzyme | 25 | phosphate | 2 |
| pure enzyme | 37 | " | 3.5 |
| pure enzyme | 25 | TES | 2.8 |
| pure enzyme | 37 | " | 3 |
| *Chainia purpurogena* | | | |
| crude extract supernatant | 37 | phosphate | 3 |
| crude extract supernatant | 37 | TES | 3 |
| *Chainia ochraceae* (DSM 43 155) | | | |
| crude extract supernatant | 37 | phosphate | 3.5 |
| crude extract supernatant | 37 | TES | 3.6 |
| *Streptomyces flocculus* (DSM 40 327) | | | |
| crude extract supernatant | 37 | TES | 3.5 |
| Bacillus sp. | 25 | phosphate | 16 |
| Bacillus sp. | 25 | TES | 20 |
| Bacillus sp. | 37 | phosphate | 18 |
| Bacillus sp. | 37 | TES | 20 |

Stressing reagent a:

0.15 mole potassium phosphate or 0.1 mole TES/KOH (pH 7.9), 8.6 mmole 2,4,6-tribromo-3-hydroxybenzoic acid, 0.8 mmole 4-aminoantipyrine, 10 μmole potassium ferrocyanide, 5 mmole sodium cholate, 0.5% Lutensol ON 50, 0.2% sodium azide, 0.5 mmole Titriplex III, 2000 U lipase, 2000 U peroxidase and 10000 U ascorbate oxidase, per liter.

The enzyme according to the present invention has a superior stability in a detergent-containing medium at 37° C. which is shown not only by the crude extract supernatant but also by the purified enzyme. The following Table II shows the stability of the enzyme according to the present invention in comparison with known sarcosine oxidases.

TABLE II

| origin of the sarcosine oxidase | % residual activity after incubation in stressing reagent b at 37° C. over different time intervals | | | |
|---|---|---|---|---|
| | 15 min. | 30 min. | 45 min. | 60 min. |
| *Pseudomonas maltophilia* | 7 | 3 | 2 | 0 |
| *Corynebacterium sp.* U96 | 6 | 2 | 1 | 0 |
| Bacillus sp. | 87 | 84 | 78 | 75 |
| Arthrobacter sp. | 7 | 1 | 0 | 0 |
| *Cylindrocarpon didymum* M-1 | 0 | 0 | 0 | 0 |
| *Chainia purpurogena* pure enzyme | 90 | 87 | 83 | 77 |
| *Chainia purpurogena* crude extract supernatant | 90 | 87 | 82 | 75 |
| *Streptomyces flocculus* crude extract supernatant | 97 | 97 | 96 | 94 |

Stressing reagent b:

0.15 mole potassium phosphate (pH 7.9), 8.6 mmole 2,4,6-tribromo-3-hydroxybenzoic acid, 0.8 mmole 4-aminoantipyrine, 10 μmole potassium ferrocyanide, 5 mmole sodium cholate, 0.5% Lutensol ON 50, 0.2% sodium azide, 0.5 mmole Titriplex III, 2000 U lipase, 2000 U peroxidase, 10000 U ascorbate oxidase, 25000 U creatininase, 12000 U creatinase, >100 U sarcosine oxidase.

The above values show that only the enzyme from Bacillus displays a comparable stability, whereas all other enzymes possess a stability which is fully insufficient for practical use.

The following Table III shows the long-term stability at 25° C. of the enzyme according to the present invention and of the Bacillus sp. enzyme.

TABLE III

| origin of the sarcosine oxidase | buffer | % residual activity after two days incubation in stressing reagent c at 25° C. |
|---|---|---|
| *Chainia purp.* pure enzyme | phosphate | 83 |
| | TES | 80 |
| *Chainia purp.* crude extract | phosphate | 86 |
| | TES | 88 |
| *Chainia ochr.* crude extract | phosphate | 75 |
| | TES | 75 |
| *Streptomyces flocc.* crude extract | phosphate | 44 |
| | TES | 35 |
| Bac. sp. pure enzyme | phosphate | 15 |
| | TES | 15 |

Stressing reagent c:

Composition as for stressing agent b but without the addition of the chromogenic colour system. Besides 0.15 mole potassium phosphate (pH 7.9), 0.1 mole TES/KOH is also used.

The above values show that the enzyme of the present invention is far superior to the best previously known sarcosine oxidase enzyme with regard to long-term stability. This is especially important for the storage stability which correlates with the long-term stability.

Therefore, because of its smaller Michaelis constant, the enzyme according to the present invention makes possible a substantially quicker carrying out of the enzymatic determination of sarcosine, creatine or creatinine. It has a very substantially better storage stability at 0° to 25° C. and, over the incubation interval, is, in the case of sarcosine, creatine or creatinine determinations at 37° C., substantially more stable than most of the known sarcosine oxidases.

The following Examples are given for the purpose of illustrating the present invention:

EXAMPLE 1

Culturing of *Chainia purpurogena* DSM 43156

The organism was cultured in a complex medium of the following composition in a shaking flask: 5 g. yeast extract, 3 g. peptone (tryptic digested), 2 g. sodium chloride, 0.24 g. magnesium sulphate heptahydrate, 0.014 g. calcium chloride heptahydrate, 2 g. glucose, 10 g. sarcosine and 1 liter water (pH 7.0). The cultures produced at 28° C. yielded, after 30 hours, an activity of about 400 U/liter.

EXAMPLE 2

Isolation of sarcosine oxidase (E.C. 1.5.3.1) from Chainia 2.9 kg. of moist mass of *Chainia purpurogena* DSM 43156 (obtained from 95 liters of culture) were suspended in 15 liters of 20 mmole/liter phosphate buffer (pH 8.0) and digested for 4 hours at 25° C. with 4 g. lysozyme. To the digestion suspension was added so much 10% polyethyleneimine (Polymin G-20) solution (BASF) that a substantial separation of nucleic acids and foreign proteins took place. The sarcosine oxidase, which was present in the supernatant, was bound to a weakly basic anion exchanger (DEAE-Sephadex) and subsequently eluted with increasing salt gradients. The eluate was adjusted with ammonium sulphate to a concentration of 0.6 mole/liter and the enzyme was bound to phenyl-Sepharose and chromatographed with drecreasing ammonium sulphate gradients (above phosphate buffer). The eluates with over 4 U/mg. of protein were adjusted with ammonium sulphate to a concentration of up to 2.4 mole/liter. The precipitate was taken up in 0.1 mole/liter phosphate buffer and the sarcosine oxidase further purified by passage over a molecular sieve (Sephacryl-S-200, Pharmacia). The purified enzyme obtained had a specific activity of 5.5 U/mg. protein.

EXAMPLE 3

Use of sarcosine oxidase for the determination of creatinine

| (a) Reagent I (sample blank reagent): | |
|---|---|
| potassium phosphate (pH 7.9) | 150 mmole/l. (or 0.1 mole/l. TES/KOH pH 7.9) |
| 4-aminoantipyrine | 0.8 mmole/l. |
| 2,4,6-tribromo-3-hydroxy-benzoic acid | 8.6 mmole/l. |
| potassium ferrocyanide | 10 μmole/l. |
| sodium cholate | 5 mmole/l. |
| Lutensol ON 50 | 0.5% (w/v) |
| creatinamidinohydrolase | 12 U/ml. |
| sarcosine oxidase according to Example 2 | 6.5 U/ml. |
| peroxidase | 2 U/ml. |
| lipase | 2 U/ml. |
| ascorbate oxidase | 10 U/ml. |
| (b) Reagent II (sample reagent): | |
| Reagent I plus creatinin-amidohydrolase | 25 U/ml. |
| (c) Carrying out of test/determination batch: | | wavelength 546 nm; T = 25° C. (or 37° C.);
layer thickness = 1 cm.
measurement against air.

| | 1. Reagent I blank | 2. sample blank | 3. Reagent II blank | 4. sample value |
|---|---|---|---|---|
| Reagent I | 1.00 ml. | 1.00 ml. | — | — |
| Reagent II | — | — | 1.00 ml. | 1.00 ml. |
| water | 0.05 ml. | — | 0.05 ml. | — |
| sample | — | 0.05 ml. | — | 0.05 ml. |

Incubate for 20 minutes at 25° or 37° C., then measure extinctions $E_1$–$E_4$.

$$E=(E_4-E_3)-(E_2-E_1).$$

Calculation of the creatinine concentration in the sample: via concurrently conducted aqueous standard (2 mg./dl.). The standard is, for this purpose, introduced into the determination batch in the same way as the sample.

We claim:

1. Hydrogen peroxide-forming sarcosine oxidase, obtained from Streptomycetaceae and at 25° C. in 0.15 mol/liter potassium phosphate (pH 7.9), in the presence of surface-active substances, still shows after 2 days an activity of at least 40% of the initial activity.

2. The sarcosine oxidase of claim 1 obtained from the species of Streptomycetaceae designated *Chainia purpurogena, Chainia ochraceae, Streptomyces flocculus,* Streptoverticillium and *Kitasatoa purpurea.*

3. A process for obtaining the sarcosine oxidase of claim 1, comprising culturing a strain of the family Streptomycetaceae having a content of sarcosine oxidase and recovering the enzyme from the biomass.

4. The process of claim 3 wherein the species of Streptomycetaceae which is cultured, is designated *Chainia purpurogena, Chainia ochraceae, Streptomyces flocculus,* Streptoverticillium and *Kitasatoa purpurea.*

* * * * *